(12) United States Patent
Sandrin (10) Patent No.: US 11,331,073 B2
(45) Date of Patent: *May 17, 2022

(54) DEVICE AND METHOD FOR MEASURING THE VISCOELASTIC PROPERTIES OF A VISCOELASTIC MEDIUM

(71) Applicant: ECHOSENS, Paris (FR)

(72) Inventor: Laurent Sandrin, Bourg-la-Reine (FR)

(73) Assignee: ECHOSENS, Paris (FR)

( * ) Notice: Subject to any disclaimer, the term of this patent is extended or adjusted under 35 U.S.C. 154(b) by 87 days.

This patent is subject to a terminal disclaimer.

(21) Appl. No.: 16/498,162

(22) PCT Filed: Mar. 26, 2018

(86) PCT No.: PCT/EP2018/057609
§ 371 (c)(1),
(2) Date: Sep. 26, 2019

(87) PCT Pub. No.: WO2018/177991
PCT Pub. Date: Oct. 4, 2018

(65) Prior Publication Data
US 2020/0029934 A1    Jan. 30, 2020

(30) Foreign Application Priority Data
Mar. 27, 2017   (EP) .................................... 17163075

(51) Int. Cl.
*A61B 8/00*    (2006.01)
*A61B 8/08*    (2006.01)

(52) U.S. Cl.
CPC ............ *A61B 8/4254* (2013.01); *A61B 8/429* (2013.01); *A61B 8/4494* (2013.01); *A61B 8/485* (2013.01)

(58) Field of Classification Search
CPC ..... A61B 8/4254; A61B 8/4494; A61B 8/485; A61B 8/543; A61B 8/08; A61B 8/429;
(Continued)

(56) References Cited

U.S. PATENT DOCUMENTS 4,213,462 A    7/1980  Sato
8,333,704 B2   12/2012 Anthony et al.
(Continued)

FOREIGN PATENT DOCUMENTS

CN    106264605 A    1/2017
EP    1 169 636 A1    1/2002
(Continued)

OTHER PUBLICATIONS

Sandrin, Laurent & Oudry, Jennifer & Bastard, Cécile & Celine, Fournier & Miette, Veronique & Mueller, Sebastian, "Non-Invasive Assessment of Liver Fibrosis by Vibration-Controlled Transient Elastography (Fibroscan)" Sep. 2011, "Liver Biopsy" Chapter 19. (Year: 2011).*

(Continued)

*Primary Examiner* — Colin T. Sakamoto
(74) *Attorney, Agent, or Firm* — Pillsbury Winthrop Shaw Pittman LLP (57) ABSTRACT

A device for vibration controlled transient elastography, in particular to quantify liver fibrosis, includes an ultrasound probe for elastography comprising a probe casing, at least one ultrasound transducer having a symmetry axis, a vibrator, and a force sensor, wherein the vibrator is arranged to induce a movement of the probe casing along the symmetry axis of the ultrasound transducer, the ultrasound transducer being bound to the probe casing with no motion of the ultrasound transducer relative to the probe casing, and wherein the device includes a signal generator configured to issue a contact ready signal when the force applied by the (Continued)

probe on the to-be-measured viscoelastic medium is greater than a minimum contact force threshold. The signal generator may further be configured to issue a measurement ready signal when the force is greater than a minimum measurement force threshold.

17 Claims, 4 Drawing Sheets

(58) Field of Classification Search
CPC ....... A61B 8/0833; A61B 8/44; A61B 8/4483; A61B 5/0053; A61B 5/6843
See application file for complete search history.

(56) References Cited

U.S. PATENT DOCUMENTS

| | | | |
|---|---|---|---|
| 9,538,982 B2* | 1/2017 | Anthony | ................. A61B 8/13 |
| 10,063,369 B1* | 8/2018 | Murphy | ................. G01D 21/02 |
| 10,575,780 B2* | 3/2020 | van den Ende | ...... A61B 5/6844 |
| 2005/0085728 A1 | 4/2005 | Fukuda | |
| 2005/0119568 A1 | 6/2005 | Salcudean | |
| 2005/0203398 A1 | 9/2005 | Sandrin et al. | |
| 2012/0123263 A1 | 5/2012 | Osaka | |
| 2012/0172710 A1* | 7/2012 | Anthony | .............. A61B 5/6843 600/411 |
| 2012/0316407 A1 | 12/2012 | Anthony et al. | |
| 2013/0197298 A1 | 8/2013 | Miller | |
| 2014/0114193 A1 | 4/2014 | Anthony et al. | |
| 2014/0148699 A1 | 5/2014 | Shim | |
| 2014/0330122 A1 | 11/2014 | Baghani | |
| 2016/0213350 A1 | 7/2016 | Lee | |
| 2017/0014098 A1 | 1/2017 | Shao et al. | |
| 2017/0095228 A1* | 4/2017 | Richard | ............... A61B 8/4438 |
| 2017/0245834 A1* | 8/2017 | Takeda | ................... A61B 8/485 |
| 2019/0192119 A1 | 6/2019 | Salcudean | |

FOREIGN PATENT DOCUMENTS

| | | |
|---|---|---|
| EP | 1 531 733 A2 | 5/2005 |
| EP | 3 095 387 A1 | 11/2016 |
| JP | 2005-013283 A | 1/2005 |
| JP | 2005-144155 A | 6/2005 |
| WO | WO 00/55616 A1 | 9/2000 |
| WO | WO 2004/016176 A2 | 2/2004 |
| WO | WO 2016/188947 A1 | 12/2016 |
| WO | WO 2018/078002 A1 | 5/2018 |

OTHER PUBLICATIONS

Gilbertson, Matthew Wright, "Handheld force-controlled ultrasound probe" 2010, Massachusetts Institute of Technology. Dept. of Mechanical Engineering (Year: 2010).*

Mellema et al., "Probe Oscillation Shear Elastography (PROSE): A High Frame-Rate Method for Two-Dimensional Ultrasound Shear Wave Elastography" IEEE Transactions on Medical Imaging, vol. 35, No. 9, Sep. 2016 (Year: 2016).*

International Search Report as issued in International Patent Application No. PCT/EP2018/057609, dated Jul. 3, 2018.

Sandrin, L., et al., "Non-Invasive Assessment of Liver Fibrosis by Vibration-Controlled Transient Elastography (Fibroscan®)," Liver Biopsy, Sep. 2011, XP055411434, 24 pages.

Nabavizadeh, A., et al., "Automated Compression Device for Viscoelasticity Imaging," IEEE Transactions on Biomedical Engineering, vol. 64, No. 7, Sep. 2016, XP011653910, pp. 1535-1546.

Non-Final Office Action as issued in U.S. Appl. No. 16/345,387, dated Jun. 23, 2021.

Notice of Allowance as issued in U.S. Appl. No. 16/345,387, dated Sep. 15, 2021.

Notice of Reasons for Refusal as issued in Japanese Patent Application No. 2019-553020, dated Mar. 8, 2022.

Shung, "Diagnostic Ultrasound: Imaging and Blood Flow Measurements" 2nd edition, 2015 (Year: 2015).

Winberg et al., "Inertial Mass Actuators, Understanding and Tuning" Eleventh International Congress on Sound and Vibration 2004, pp. 331-338 (Year: 2004).

Ferraioli, G., et al., "WFUMB Guidelines and Recommendations for Clinical Use of Ultrasound Elastography Part 3: Liver," Ultrasound in Med. & Biol., pp. 1-19, 2015.

Sandrin, L., et al., "Shear Elasticity Probe for Soft Tissues with 1-D Transient Elastography," IEEE Transactions on Ultrasonics, Ferroelectrics, and Frequency Control, vol. 49, No. 4, Apr. 2002, pp. 436-446.

* cited by examiner

DEVICE AND METHOD FOR MEASURING THE VISCOELASTIC PROPERTIES OF A VISCOELASTIC MEDIUM

CROSS REFERENCE TO RELATED APPLICATIONS

This application is the U.S. National Stage of PCT/EP2018/057609, filed Mar. 26, 2018, which in turn claims priority to European Patent Application No. 17163075.9 filed Mar. 27, 2017, the entire contents of all applications are incorporated herein by reference in their entireties.

FIELD OF THE INVENTION

The present invention relates to a device for measuring the viscoelastic properties of a viscoelastic medium such as a human or an animal organ. More specifically, the present invention can be used to measure the viscoelastic properties of a liver which permits to quantify the amount of fibrosis present in said liver. The invention also concerns a method for measuring the viscoelastic properties of a viscoelastic medium.

BACKGROUND

Chronic hepatitis, which can be of alcoholic, viral or other origin, has a fibrotic effect that it is important to evaluate so that to determine the best time to treat the hepatitis.

One of the most reliable and efficient techniques to measure liver stiffness is transient elastography (see for example "WFUMB guidelines and recommendations for clinical use of ultrasound elastography part 3: liver" by G. Ferraioli et al. published in "Ultrasound in Med. And Biol.", 41, 5, 2015).

The applicant has developed and commercialized a device called Fibroscan® (see for example patents EP1169636 and EP1531733). This device measures the stiffness of the liver by using an elastography technique called "Vibration Controlled Transient Elastography" (VCTE) developed by the applicant.

In a VCTE application, the measure of the liver stiffness relies on the measure of a transient shear wave propagation speed inside the tissue.

In order to perform such a measurement, a particular probe has been developed. Said probe comprises at least an electrodynamical actuator and at least an ultrasound transducer mounted on the tip of the probe.

For example, in the Fibroscan® probe, the vibrator moves the ultrasound transducer and pushes it against the patient body. This pulsed movement generates a transient shear wave which propagates inside the liver. The displacement generated by the propagating shear wave is probed by sending high frequency ultrasound short pulses or shots inside the medium.

Figure 1A:
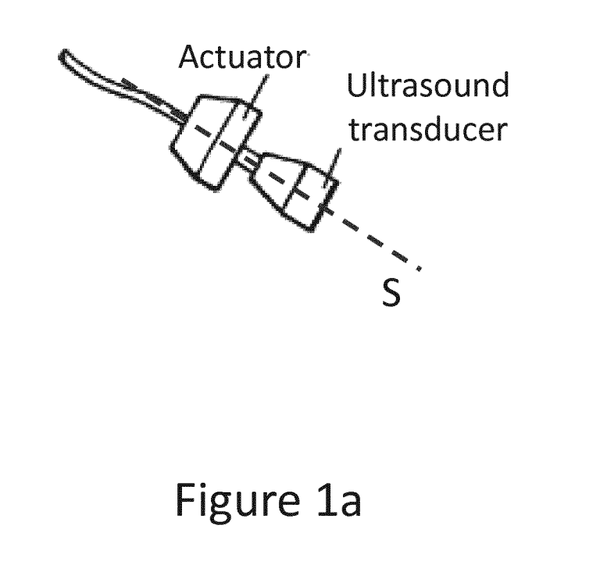
FIG. 1a represents a transient elastography device according to the prior art.

Thanks to the advantageous geometry used by the Fibroscan® (see for example FIG. 1a) the mechanical actuator and the ultrasound transducer share the same symmetry axis, as indicated by the dashed line of FIG. 1a. This geometrical arrangement makes it possible to avoid systematic errors in the measurement of the shear wave propagation speed: the shear wave and the ultrasound shots propagate along the same direction.

Moreover, the Fibroscan® probe comes with a motion sensor capable of measuring the displacement of the probe tip with respect to the probe casing, for example a Hall effect position sensor. A measurement is validated only if the tip trajectory follows a predetermined profile, for example a period of sinusoid. In traditional VCTE probe only the relative movement of the probe tip with respect to the probe casing is measured. In other words, in a traditional VCTE probe the movement of the probe tip is measured in the reference frame of the probe casing.

A relevant problem in currently available VCTE probes is the control of the real movement of the probe tip when applying the transient shear wave to the tissue to be examined. For example, when the shear wave is applied, the recoil of the probe can add to the movement of the tip and the applied pulse can be deformed. This problem is related to the recoil of the operator's hand and to the control of the force which the operator has to apply in holding the probe against the patient's body: for a correct use of a VCTE probe according to the prior art a skilled or qualified operator is needed.

If the probe recoil is not controlled, the real movement of the tip of the probe with respect to the patient's body is unknown. The measurement can be dependent upon the force applied by the operator during the generation of the shear wave.

Figure 1B:
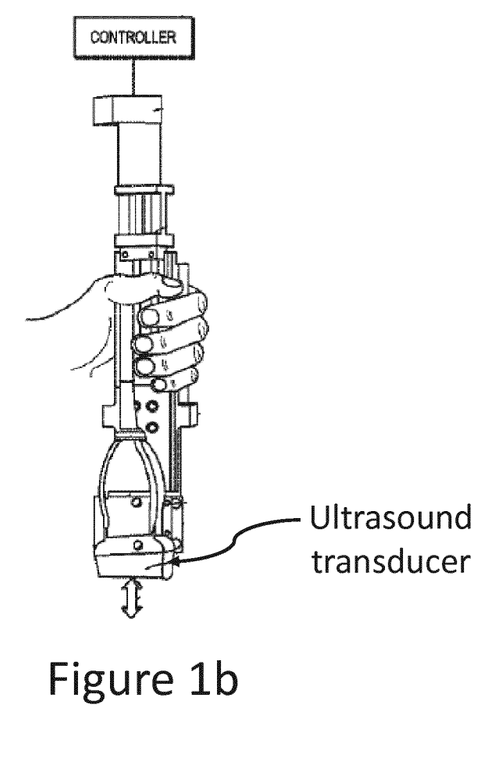
FIG. 1b represents a force controlled ultrasound probe according to the prior art.

An ultrasound probe comprising a linear actuator and a force sensor is disclosed by patent applications U.S. Pat. No. 8,333,704 B2 ("Hand-held force-controlled ultrasound probe" filed by Anthony et al. on Dec. 18, 2010) and US 2012/0316407 A1 ("Sonographer fatigue monitoring" filed by Anthony et al. on Jun. 12, 2012). FIG. 1b illustrates the device described by the document U.S. Pat. No. 8,333,704. According to these documents, the ultrasound transducer is moved by an electrodynamical actuator in order to control the force applied against the tissue to be analyzed. The movement of the ultrasound transducer is controlled based on the signal provided by the force sensor and used as a feedback signal.

These documents solve the problem of applying a constant or a time-dependent force during an ultrasound measurement but the disclosed technical solutions have several drawbacks.

For example these devices described in the prior art comprise an external mechanical mobile part: as it is shown by the arrow in FIG. 1b the ultrasound transducer is moved with respect to the probe casing. Several drawbacks are associated to this external moving part, for example the need for frequent calibration operation.

Another solution described in the prior art is described in the document "Probe Oscillation Shear Elastography (PROSE): A high Frame-Rate Method for Two-dimensional ultrasound shear wave elastography" by D. Mellema et al. (published in IEEE Transaction on medical imaging, Vol. 35, No 9, September 2016). In this case a probe for continuous wave elastography is described. This solution is not adapted for the application of a transient shear pulse to the tissue but only for continuous wave shear wave oscillation. Moreover the described elastography probe is formed by two separate components, which is a severe drawback for the in-vivo applications. For example the described probe is difficult to manipulate due to the presence of several parts.

Moreover, according to operators, when the ultrasound transducer is placed on the patient's body, it is difficult to control the applied force. Thus, such a device does not permit accurate and reproducible measurements regardless of the operator.

Moreover, if the applied force on the patient's body is too high, the electrodynamic actuator of the device may be damaged.

Finally, the acoustic power delivered to patients by the ultrasound transducer of the sensor can be high and unnecessarily used which can lead to patient injury, electronic damage and ultrasound transducer premature failure.

SUMMARY

An aspect of the invention is directed to a device that overcomes the aforementioned drawbacks. Accordingly, an aspect of the invention is directed to a device for accurate and reproducible measurements of the viscoelastic properties of a viscoelastic medium which limits health's risks for patients and prolongs the lifetime of the device.

To achieve this, a first aspect of the present invention is directed to a device for measuring viscoelastic properties of a viscoelastic medium having an ultrasound signal after being subjected to ultrasound pulses comprising:
  a probe for transient elastography comprising:
    a probe casing;
    at least one ultrasound transducer having a symmetry axis;
    at least a vibrator, said vibrator being located inside the probe casing;
    a force sensor, the force sensor being configured to measure a force applied by the probe against the to-be-measured viscoelastic medium;
  a signal generator;
  the device being characterized in that:
    the vibrator is arranged to induce a movement of the probe casing along a predefined axis, the predefined axis being the symmetry axis of the ultrasound transducer;
    the ultrasound transducer is bound to the probe casing with no motion of the ultrasound transducer with respect to the probe casing;
    the signal generator is constructed and arranged to issue a contact ready signal when the ultrasound transducer of the probe is in contact with a to-be-measured viscoelastic medium, the contact ready signal being set by the signal generator when the force applied by the ultrasound probe on the viscoelastic medium is greater than a minimum contact force threshold.

A probe casing is the enclosure of the VCTE probe, said enclosure containing a vibrator or electrodynamical actuator. The probe casing can contain also other elements as a position sensor, logic circuits or connecting means in order to store data or exchanging data with a computer or other electronic devices. An ultrasound transducer is a device adapted to emit and receive ultrasound waves. It is formed by a single transducer or by an array of transducers, forming for example a linear detector.

A symmetry axis of the ultrasound transducer is an axis of geometrical symmetry of the transducer. The symmetry axis of the ultrasound transducer is also the direction along which the ultrasounds are emitted by the transducer. The symmetry axis of the transducer corresponds to the propagation direction of the ultrasound short pulses emitted by the transducer.

According to the present invention, the ultrasound transducer is bound in motion to the probe casing, which means that there is no relative movement of the ultrasound transducer with respect to the probe casing.

An extremity of the ultrasound transducer can be fixed to an extremity of the probe casing. Another extremity of the ultrasound transducer is free to vibrate in order to transmit the ultrasound waves to the medium to analyze.

Alternatively, the ultrasound transducer can be attached to the probe casing by means of a probe tip. When present, the probe tip has an extremity fixed to one extremity of the probe casing and another extremity fixed to the ultrasound transducer.

The explication of the invention given in the following paragraphs holds both when the ultrasound transducer is fixed directly to the probe casing and when the ultrasound transducer is fixed to the probe casing through a probe tip. These two configurations are given only as exemplary embodiments and other configurations are possible.

A vibrator is a device adapted to move a mass inside a probe casing. For example the vibrator can oscillate a mass at a frequency comprised between 1 and 5000 Hz.

The probe according to the invention can be considered as an inertial probe because the movement of the probe itself is generated by the movement of a mass inside the probe casing. The probe according to the invention comprises no external mechanical moving part.

The probe according to the invention is a transient elastography probe. This means that it is adapted to both applying a transient shear wave to the tissue to detect and analyze the propagation of the shear wave by sending ultrasound short pulses at high repetition rate.

The shear wave is generated in the tissue by the movement of the probe, which pushes the ultrasound transducer against the tissue itself. The shear wave is generated by applying a low frequency pulse to the surface of the medium. For example, the pulse can have the shape of one period of a sinusoid at a central frequency f comprised between 1 Hz and 5000 Hz.

The duration of the low frequency pulse applied to the tissue is comprised between $1/2f$ and $20/f$.

Ultrasound short pulses are emitted at a repetition rate comprised between 100 Hz and $100*10^3$ Hz.

The propagation of the shear wave is detected by sending ultrasound pulses or shots at high repetition rate inside the medium and by detecting the backscattered ultrasound signals. In fact the tissue contains inhomogeneity or particles capable of partially reflecting the ultrasound pulses.

By recording and analyzing subsequent backscattered signals it is possible to compute the displacement of the tissue due to the propagation of the shear wave. The properties of the shear wave can then be deduced. For example, the propagation speed of the shear wave is directly related to the stiffness of the viscoelastic medium.

An advantage of the probe described in the present invention is to control the real movement of ultrasound transducer. In fact, the ultrasound transducer is bound to the probe casing and there is no reciprocal movement between the ultrasound transducer and the probe casing. It is then possible to monitor the movement of the probe casing, which corresponds to the real movement of the ultrasound transducer. Measuring the real movement of the ultrasound transducer is important in order to control the shape of the transient shear wave generated inside the tissue. For example the movement of the probe can be measured with an accelerometer mounted on the probe itself.

In other words, according to the present invention, the movement of the ultrasound transducer is measured in the reference frame of the earth, in contrast to what is done in a traditional VCTE probe. In fact in a VCTE probe according to the prior art, the movement of the ultrasound transducer is measured in the reference frame of the probe casing and only the relative movement of the ultrasound transducer with respect to the probe casing is measured.

In practice, the motion of the mass actuated by the vibrator inside the probe casing can be determined by a control loop using the movement of the probe casing as a feedback signal. This makes it possible to directly compensate the motion of the hand of the operator during the application of the shear wave.

There is no need for the operator to apply a precise force in order to compensate the recoil of the probe. As a consequence, performing a measure of stiffness on a viscoelastic medium becomes easier for the operator of the probe. Moreover, the measured values of stiffness are more reproducible.

By measuring only the relative movement of ultrasound transducer with respect to the probe casing, as it is done in the prior art, it would not be possible to take into account the recoil of the probe. As a consequence, even if the relative movement of the tip follows a sinusoidal trajectory, the effective low frequency pulse applied to the patient body can have a different shape due to the recoil of the probe.

According to the present invention the ultrasound transducer in contact with the patient's body moves together with the probe casing. Detecting the probe casing movement is equivalent to detecting the probe tip movement. The probe casing movement is used as a feedback for the vibrator. In fact the amplitude of the oscillation of the vibrator can be adjusted in order to obtain the desired movement of the probe tip in contact with the patient's body. Moreover, the lack of external moving part in the probe according to the invention removes the need for frequent mechanical calibration.

As the device of the invention comprises a signal generator that issues a contact ready signal, the operator does not activate the ultrasound signals unless the signal generator issues a contact ready signal. Thus, said device guarantees that the ultrasound signal power emitted by the ultrasound transducer is used only when necessary and is as low as possible for the patient.

Said contact ready signal is issued by the signal generator based on the contact force between the ultrasound transducer and the patient's body. The contact force can be measured by a force sensor placed on the probe. The contact ready signal is issued only if the measured contact force meets a predefined condition. For example, the measured contact force must be greater than a minimum contact force threshold. When such a condition is met the probe is considered in contact with the to-be-measured viscoelastic medium. Alternatively, the contact ready signal can be issued only if the contact force is comprised between a minimum contact force threshold and a maximum contact force threshold.

Moreover, considering that the contact ready signal is set only when the transducer of the ultrasound probe is in contact with the to-be-measured viscoelastic medium, the device's measurements are accurate and reproducible regardless of the device's operator. In fact, with the device of the prior art, the operator can generate ultrasound signals even when the transducer attached to the tip of the ultrasound probe is not in contact with the to-be-measured medium, which causes inaccurate or false measurements. Indeed, the measurements realized with the device of the prior art depend on the operator and more particularly on the contact of the probe against the patient's body.

In addition to the contact ready signal, the device according to the invention is constructed to emit a measurement ready signal. The measurement ready signal is emitted only when the contact force between the US transducer and the tissue is comprised between a minimum and a maximum measurement force threshold. When this condition is verified, the measurement ready signal is issued and a viscoelastic measurement is triggered, automatically or manually. In other words, a low frequency pulse is applied to the tissue only if the measurement ready signal is issued.

The device according to the first aspect of the invention may also have one or more of the features below, considered individually or according to all of the technically possible combination:

The signal generator is constructed and arranged to issue a measurement ready signal;

The force sensor is constructed and arranged to measure a force applied by the ultrasound probe against the to-be-measured viscoelastic medium, the contact ready signal being set by the signal generator when the force applied by the ultrasound probe on the viscoelastic medium is greater than a minimum contact force threshold and the measurement ready signal being set by the signal generator when the force applied by the ultrasound probe is greater than a minimum measurement force threshold;

the minimum contact force threshold is comprised between 0.1 N and 1.0 N;

the minimum measurement force threshold is comprised between 1.0 N and 6.0 N;

the measurement ready signal is set by the signal generator when the force applied by the ultrasound probe on the viscoelastic medium is smaller than a maximum measurement force threshold;

the maximum measurement force threshold is comprised between 6.0 N and 20.0 N;

The minimum contact force threshold is equal to 0.5 N;

The minimum measurement force threshold is equal to 4.0 N;

The maximum measurement force threshold is equal to 8.0 N;

The contact ready signal is set when the force measured by the force sensor is comprised between a minimum contact force threshold and a maximum contact force threshold;

The device according to one of the previous claims characterized in that the ultrasound transducer is bound to the probe casing by means of a probe tip, said probe tip having a first extremity fixed to the probe casing and a second extremity fixed to the ultrasound transducer;

The device according to the previous claim characterized in that the probe tip is interchangeable;

The probe comprises a position sensor and the device comprises a control loop configured to control the vibrator based on the signal received from the position sensor;

the force sensor is a capacitive sensor or an applied force sensor;

the device comprises means to trigger a measurement of a viscoelastic property of a viscoelastic medium only if a measurement ready signal is set; these means comprise an electronic microchip or an electronic microprocessor receiving the contact ready signal and the measurement ready signal; if an acquisition is required, the microchip or microprocessor triggers the measure of a viscoelastic property when the measurement ready signal is set;

the vibrator or electrodynamic actuator is constructed and arranged to generate low-frequency impulse displacements of the ultrasound probe only when the measurement ready signal is set;

the force sensor comprised in the probe is constructed and arranged to measure a force applied by the ultrasound probe against the to-be-measured viscoelastic medium, the contact ready signal and/or the measurement ready signal being set by the signal generator when the force measured by the force sensor is:
  for the contact ready signal, superior to a minimum force contact threshold,
  for the measurement ready signal, superior to a minimum force measurement threshold. Further, in a not limited embodiment, the measurement ready signal is set when the force measured by the force detecting module, is inferior to a maximum force measurement threshold;
The ultrasound transducer is constructed and arranged to activate the emission of the ultrasound signals when the contact ready signal is set;
The device comprises a display unit which displays ultrasound images, the display unit being constructed and arranged to refresh ultrasound images only when the contact ready signal is set;
The device comprises guidance indicators constructed and arranged to refresh only when the contact ready signal is set;
The ultrasound probe comprises at least one light-emitting diode, the ultrasound probe being constructed and arranged to light the light-emitting diode only when the contact ready signal is set;
The device comprises device commands, the access to the device commands being possible only when the contact ready signal is set;
The device is constructed and arranged to deactivate a combined modality of said device when the contact ready signal is set;
The device is constructed and arranged to activate a combined modality of said device when the contact ready signal is set;
The ultrasound transducer is bound to the probe casing by means of a probe tip, said probe tip having a first extremity fixed to the probe casing and a second extremity fixed to the ultrasound transducer;
The device is constructed and arranged to trigger the application of a low frequency pulse to the to-be-measured viscoelastic medium only if the measurement ready signal is set;
The probe comprises a position sensor and the device comprises a control loop configured to control the vibrator based on the signal received from the position sensor;
The force sensor is a capacitive sensor or an applied force sensor;

A second aspect of the present invention is directed to a method for measuring viscoelastic properties of a viscoelastic medium having an ultrasound signal after being subjected to ultrasound impulses comprising the following steps:
  positioning of an ultrasound transducer of an ultrasound probe in contact with a to-be-measured viscoelastic medium,
  generating a contact ready signal when the transducer of the ultrasound probe is in contact with the to-be-measured viscoelastic medium, the contact ready signal being issued by a signal generator constructed and arranged to issue a contact ready signal.

The method according to one aspect of the invention may also have one or more of the features below, considered individually or according to all of the technically possible combination:
  The method comprises a further step of measuring a force applied by the ultrasound probe against the to-be-measured viscoelastic medium, the measurement of a force being determined by a force sensor constructed and arranged to measure a force applied by the ultrasound probe against a to-be-measured viscoelastic medium, the contact ready signal being set by the signal generator when the force exerted by the ultrasound probe is higher than a minimum contact force threshold and the measurement ready signal being set by the signal generator when the force applied by the ultrasound probe is higher than a minimum measurement force threshold or comprised between a minimum and a maximum measurement force threshold.
  The method comprises a step of emitting ultrasound pulses only when the contact ready signal is issued;
  The method comprises a step of displaying localization means only if the contact ready signal is issued; localization means are tools used by an operator in order to locate the to-be-measured viscoelastic tissue; example of localization means are imaging, guidance tools or other indicators;
  The method comprises a step of refreshing images only if the contact ready signal is issued;
  The method comprises a step of refreshing the guidance tools only if the contact ready signal is issued;
  The method comprises a step of accessing the memory of the device only if the contact ready signal is issued;
  The method comprises a step of setting on a led only when the contact ready signal and the measurement ready signal are set;
  The method comprises a step of triggering a measurement of a viscoelastic properties only when the contact ready signal and the measurement ready signal are set;
  The method comprises a step of accessing a command only when the contact ready signal and the measurement ready signal are set;
  The method comprises a step of deactivate other modality when the contact ready signal is issued and a step of activate other modality when the contact ready signal is not issued;

BRIEF DESCRIPTION OF THE DRAWINGS

The accompanying drawings are included to provide a further understanding of the invention and are incorporated in a constitute part of this specification, to illustrate aspects of the invention and, together with the description, to explain the principles of the invention.

DESCRIPTION OF SPECIFIC EMBODIMENTS

This invention provides, in a first aspect, a device DEV for measuring the viscoelastic properties of a viscoelastic medium having an ultrasound signal after ultrasound illumination. More particularly, the device DEV of the invention permits to quantify instantaneously and in a non-invasive manner a liver fibrosis.

Figure 2:
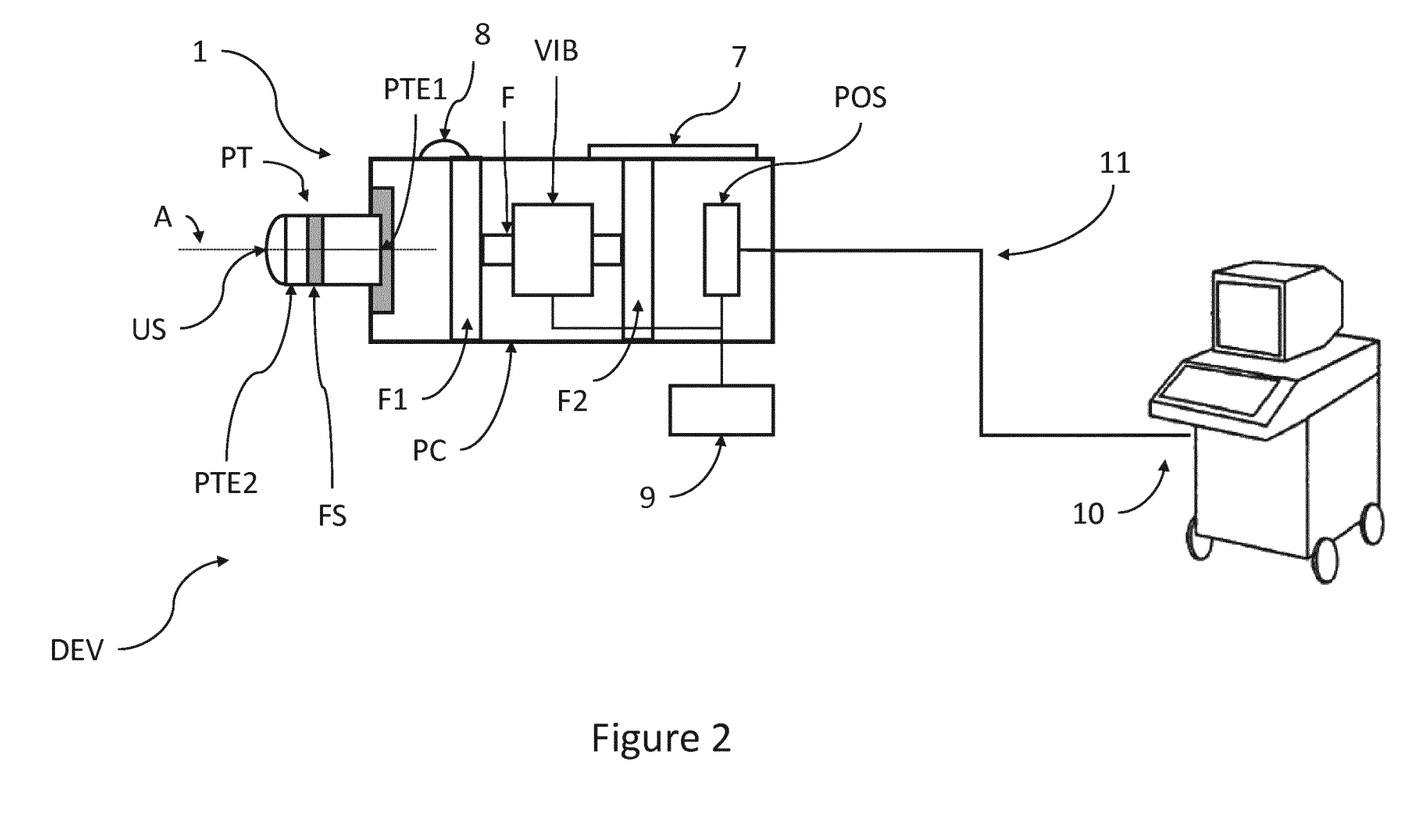
FIG. 2 represents an example of a device for measuring the viscoelastic properties of a viscoelastic medium according to an aspect of the invention.

According to an example selected to illustrate an aspect of the invention and illustrated in FIG. 2, the device DEV comprises an ultrasound probe 1. FIG. 2 shows a sectional view of the probe 1.

The ultrasound probe 1 comprises:
- a probe casing PC containing at least a vibrator or an electrodynamical actuator VIB; in a particular embodiment the vibrator VIB comprises a fixed part FIX and a mobile part MOV;
- a first vertical bar F1, a second vertical bar F2 and a horizontal bar F configured to fix the fixed part FIX of the vibrator VIB to the probe casing PC;
- an ultrasound transducer US having a symmetry axis A;
- a position sensor POS comprising an accelerometer ACC and configured to measure the position or the displacement of the probe casing PC as a function of time, said position sensor cooperating with a control loop analyzing the data provided by the position sensor POS and controlling the vibrator VIB; the position sensor is used to control the vibration of the probe as a function of acceleration, speed or preferably, displacement or position;
- a probe tip PT having a first extremity PTE1 fixed to the front end of the probe casing PC and a second extremity PTE2 fixed to the ultrasound transducer US, the front end of the probe casing PC being the extremity of the probe casing which is placed at proximity of the tissue;
- a force sensor FS placed on the probe tip PT and in proximity of the ultrasound transducer US, in between the probe tip and the rest of the probe, said force sensor FS being connected to a signal generator 9 by connecting means not showed in FIG. 1; the force sensor FS is constructed and arranged to measure the contact force exerted by the probe 1 on the viscoelastic tissue to be measured;
- connecting means for connecting the position sensor POS to the control loop and to the vibrator VIB, connecting means for connecting the ultrasound transducer US and the force sensor FS with the other components of the device DEV;
- a display unit 7 constructed and arranged to display ultrasound images,
- a push-button 8 constructed and arranged to turn on the ultrasound probe 1,
- a signal generator 9 constructed and arranged to issue a contact ready signal or a measurement ready signal or both a contact ready signal and a measurement ready signal.

The device DEV further comprises:
- device commands 10 constructed and arranged to control the device DEV by an operator,
- a cable 11 constructed and arranged to link the ultrasound probe 1 to the device commands 10.

In the following description, we will take the example of a liver as the viscoelastic medium whose viscoelastic properties are measured.

As specified, the signal generator 9 of the device DEV of the invention is constructed and arranged to emit a contact ready signal when the transducer US of the ultrasound probe 1 is in contact with the to-be measured viscoelastic medium. The generation of the contact ready signal makes it possible to obtain accurate and reproducible measurements of the viscoelastic properties of a liver regardless of the device's operator.

According to an aspect of the invention, the contact ready signal is determined by using the force sensor FS. Actually, a contact ready signal is generated by the signal generator 9 when the force applied by the ultrasound probe 1 against the patient's skin is greater than a minimum contact force threshold. More particularly, the force sensor FS is adapted to measure the force exerted by the probe 1 against the patient's skin.

According to an embodiment, the contact ready signal is issued by the signal generator 9 when the force measured by the force sensor FS is greater than a minimum contact force threshold.

According to an embodiment the minimum contact force threshold is comprised between 0.1 N and 1 N.

According to an embodiment the minimum threshold for the contact force is 0.5 N. This minimum force level is used to detect a contact between the tip of the probe and the to-be-measured viscoelastic tissue.

Advantageously, the use of a minimum contact force threshold makes it possible to control the contact between the probe and the viscoelastic medium in order to avoid, for example, the emission of ultrasounds when the probe is not used.

According to an embodiment, the contact ready signal is issued by the signal generator 9 when the force measured by the force sensor FS is smaller than a maximum contact force threshold.

Advantageously, the contact ready signal makes it possible to prevent the operator from applying an excessive force against the patient's body and therefore hurting the patient.

Advantageously, the contact ready signal makes it possible to prevent the damaging of the probe 1 due to the high force exerted against the patient's body.

According to an embodiment, the measurement ready signal is issued by the signal generator 9 when the force measured by the force sensor FS is greater than a minimum measurement force threshold.

Advantageously, the minimum measurement force threshold is necessary in order to efficiently transmit a shear wave into the viscoelastic medium and to obtain a reliable measurement of the viscoelastic properties of the tissue.

According to an embodiment of the present invention the measurement ready signal is issued by the signal generator 9 when the force measured by the force sensor FS is comprised between a minimum measurement force threshold and a maximum measurement force threshold.

According to an embodiment the minimum measurement force threshold is comprised between 1.0 and 6.0 N and the maximum measurement force threshold is comprised between 6.0 N and 20.0 N.

Advantageously this range of force thresholds makes it possible to adapt the measurement conditions to the size of the ultrasound transducer and to the body-type of the patient. For example in the case of an obese patient a larger ultrasound probe and higher force thresholds can be chosen in order to correctly apply a low frequency pulse for an elastography measurement.

According to an embodiment, the minimum measurement force threshold is equal to 4 N and the maximum measurement force threshold is equal to 8 N.

A viscoelastic measurement is triggered only if the measurement ready signal is issued by the signal generator 9. Advantageously, when the condition on the measurement force threshold is verified and the measurement ready signal is issued, the low frequency pulse is efficiently applied to the viscoelastic tissue and its shape is precisely controlled.

The device DEV comprises means to trigger a measurement of a viscoelastic property of a viscoelastic medium only if a measurement ready signal is set; these means comprise an electronic microchip or an electronic microprocessor receiving the contact ready signal and the measurement ready signal; if an acquisition is required, the microchip or microprocessor triggers the measure of a viscoelastic property when the measurement ready signal is set. The means to trigger a measurement can be embedded in the device commands 10.

Advantageously, when the condition on the measurement force threshold is verified and the measurement ready signal is issued, the shear wave is efficiently induced into the patient's body given that the impedance is matched in between the subcutaneous tissues and the liver.

According to an embodiment of the present invention the force sensor FS is a capacitive sensor or an applied force sensor.

An advantage of this embodiment is to precisely measure the force exerted from the probe 1 against the patient's body.

According to an embodiment of the present invention the probe 1 comprises a position sensor POS and the device DEV comprises a control loop configured to control the vibrator (VIB) based on the signal received from the position sensor (POS).

The control loop can be embedded in the probe 1 or in the device commands 10. In practice the control loop sets the motion parameters of the vibrator VIB in order to obtain a target low frequency pulse. The position of the probe 1 as measured by the position sensor POS is used as a feedback signal for the control loop.

An advantage of this embodiment is to precisely control the shape of the low frequency pulse applied to the patient's body. Moreover the probe 1 has no external moving parts which eliminates the need for frequent mechanical calibrations.

Figure 3:
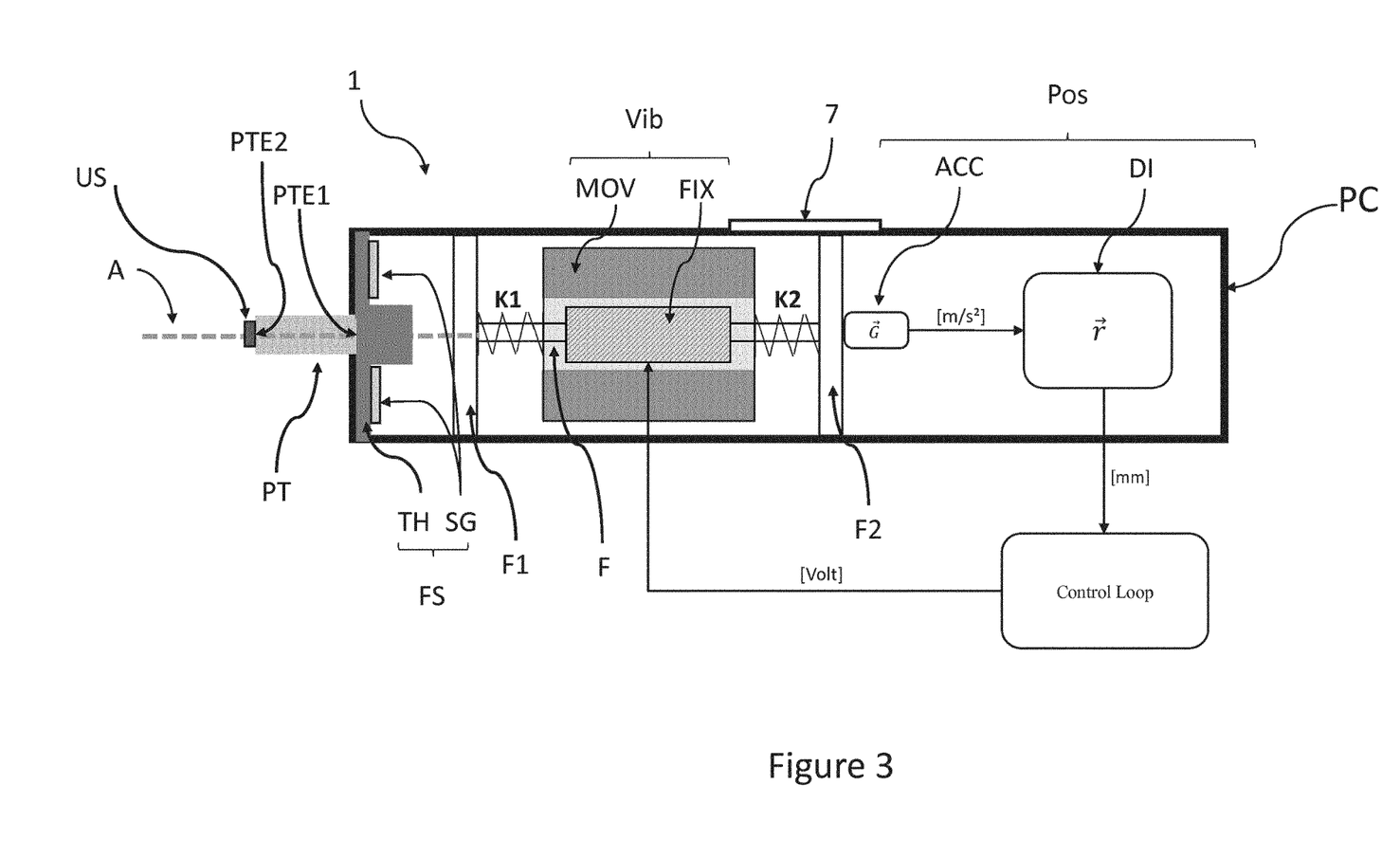
FIG. 3 represents an embodiment of the device according to FIG. 2.

FIG. 3 is a detailed representation of a sectional view of probe 1 further comprising a first spring K1 extending from the first bar F1 to the mobile part MOV and a second spring K2 extending from the second bar F2 to the mobile part MOV;

According to an embodiment, the probe casing PC has a cylindrical shape, the axis A being the axis of the cylinder. Alternatively, the probe casing can have the shape of a solid of revolution having axis A.

The size of the probe casing is chosen in order to obtain a handheld probe. According to the embodiment the circumference of the cylinder is comprised between 120 mm and 160 mm.

The axis A is the symmetry axis of the ultrasound transducer US. For example in the case of a cylindrical ultrasound transducer the axis A is the axis of the cylinder forming the transducer. The axis A identifies also the propagation direction of the ultrasound short pulses emitted by the ultrasound transducer US.

According to another embodiment, the probe casing PC can have any shape adapted to be held by the operator's hand during the measurement. For example the probe casing PC can have the shape of a standard echography probe as it is showed in FIG. 5.

The vibrator VIB is placed inside the probe casing PC and it is formed by two elements: a mobile mass MOV and a fixed element FIX. The vibrator VIB is configured to set the mass MOV in motion, which generates the motion of the whole probe 1 along the axis A.

We define as vertical a direction normal to the axis A and as horizontal a direction parallel to the axis A.

According to an embodiment, the fixed part FIX is held in place by the holding means formed by a first vertical bar F1, a horizontal support bar F and a second vertical bar F2. The first and second vertical bars F1 and F2 are fixed to the probe casing. The horizontal support bar F extends from the first vertical bar F1 to the second vertical bar F2.

Alternatively, only one vertical bar, F1 or F2, can be present in order to support the horizontal bar F and the vibrator VIB.

The holding means F1, F and F2 block the fixed part FIX that is then bound to the probe casing PC. Any other configuration of holding means adapted to bind the fixed part FIX of the vibrator VIB to the probe casing PC can be used.

The mobile part MOV is separated from the first and second vertical bars, respectively F1 and F2, by two springs, respectively K1 and K2. The first spring K1 extends from the first vertical bar F1 to the moving part MOV, the second spring extends from the second vertical bar F2 to the moving part MOV.

When actuated by the vibrator VIB, the moving part MOV slides along the horizontal bar F. The horizontal bar F supports both the fixed part FIX and the mobile part MOV of the vibrator VIB.

The two springs K1 and K2 support the moving part MOV and act as a recalling force when the moving part MOV is set in motion.

It is worth to note that the moving part MOV oscillates inside the probe casing PC. The vibrator VIB does not move any external part of the inertial probe 1.

According to the embodiment represented in FIG. 2, the mobile mass MOV is a permanent magnet and the fixed part FIX is a coil. When an electric potential is applied to the coil FIX, a force is exerted between the coil FIX and the magnet MOV and an oscillation of the mass MOV along the axis A is produced.

The movement of the probe casing PC is induced by the movement of the moving part MOV due to both the action of the electromagnetic force between the coil and the magnet and the recalling force exerted by the springs K1 and K2. This movement can be described as consequence of the law of conservation of momentum, the movement of the moving part MOV determining the recoil of the probe casing PC.

As a result, the whole inertial probe 1 is set in motion and the ultrasound transducer US is pushed against the patient's body.

An advantage of this configuration is that the movement of the ultrasound transducer US against the tissue to analyze is directly determined by the vibrator VIB and it can be accurately controlled. In other words, given the absence of relative movement of the ultrasound transducer US with respect to the probe casing PC, the amplitude of the displacement of the ultrasound transducer US coincides with the amplitude of the movement of the probe casing PC. The shape of the low frequency pulse applied to the tissue is then accurately controlled.

According to the invention, there are several possible solutions to fix the ultrasound transducer US to the probe casing PC.

According to an embodiment, the ultrasound transducer US can be directly fixed to the probe casing PC. Alternatively the ultrasound transducer US can be fixed to a force sensor FS which is in turn attached to the probe casing PC.

An advantage of this embodiment is that this configuration is simple to realize. Moreover the force sensor FS is directly in contact with the ultrasound transducer US, which makes the detection of the probe casing PC deformation more efficient. The deformation of the probe casing PC is a micrometric deformation and it is due to the contact between the ultrasound transducer US and the tissue to be analyzed.

According to the embodiment represented in FIG. 2, the ultrasound transducer US is fixed to a probe tip PT which comprises a first extremity PTE1. The first extremity PTE1 is fixed to the front end of the probe casing PC. For example the probe tip PT has a sensibly cylindrical shape as it is shown in FIG. 1.

For example, the probe tip PT can be secured to the probe casing PC by inserting the first extremity of the probe tip PTE1 inside a housing HOU present in the force sensor FS, as it is showed in FIG. 2. The second extremity of the probe tip PTE2 is fixed to the ultrasound transducer US.

An advantage of this embodiment is that the probe tip PT is easily interchangeable. In other words it is possible to use different probe tips PT having different ultrasound transducer US, in order to adapt the properties of the emitted ultrasound shots to the properties of the tissue or of the patient's body.

According to an embodiment, the motion of the inertial probe 1 is measured by means of a position sensor POS.

An advantage of this embodiment is the direct measurement of the amplitude of the movement of the probe casing PC, which is identical to the amplitude of the movement of the ultrasound transducer US. In fact according to the invention no movement of the ultrasound transducer US with respect to the probe casing PC is possible. In other words, the ultrasound transducer US is at rest in the reference frame of the probe casing PC.

In the embodiment represented in FIG. 3 the position sensor POS is formed by an accelerometer ACC and an electronic circuit DI performing a double temporal integration. The double integrator DI gives the position r of the probe starting from the measured acceleration.

Any electronic circuit capable of computing the position r from the measured acceleration can be used in the present invention.

Advantageously, the position sensor POS provides a direct measurement of the displacement of the ultrasound transducer US. In other words the position sensor POS directly measures the shape of the low-frequency pulse applied to the tissue in order to generate the transient shear wave inside the tissue.

The probe 1 is then adapted to cooperate with a control loop capable of driving the vibrator VIB in order to obtain a predefined low frequency pulse shape. The control loop can for example be embedded in a Fibroscan® device.

The position r measured by the position sensor POS is then used as a feedback signal for controlling the vibrator VIB. According to an embodiment, the position r is fed to a control loop which controls the amplitude and frequency of the oscillation of the moving mass MOV.

Thanks to this arrangement, the movement of the ultrasound transducer US can be directly controlled and a well-defined low frequency pulse is applied to the patient's body.

According to the embodiment showed in FIG. 3 the probe 1 comprises also connecting means for transmitting the electrical signals between the position sensor POS, the control loop and the vibrator VIB. The connecting means comprise also means for delivering the electrical power necessary in order to operate the vibrator VIB, the ultrasound transducer US and the other embedded equipment. The power delivering means are not showed in FIG. 3.

According to the embodiment showed in FIG. 3, the force sensor FS is a tip holder TH equipped with at least one strain gauge SG or another stress sensor. The force sensor of FIG. 3 is further adapted to receive and secure an extremity of the probe tip PT.

According to an embodiment, the means connecting the position sensor POS, the control loop and the vibrator VIB can be wireless.

An advantage of the invention is the possibility to define and carefully control the low frequency pulse applied to the tissue. The real movement of the ultrasound transducer US is measured by the position sensor POS. The oscillation properties of the moving mass MOV are adjusted by the control loop in order to apply the target low frequency pulse shape to the patient's body.

In a typical transient elastography application, the low frequency pulse applied to the patient's body has a sinusoidal shape, with a central frequency comprised between 1 Hz and 5000 Hz, a peak-to-peak amplitude comprised between 10 µm and 20 mm and a duration comprised between 100 µs and 20 s. The repetition rate for the ultrasound pulses is comprised between 100 Hz and 100000 Hz.

According to an embodiment the peak-to-peak amplitude is comprised between 50 µm and 5 mm.

The movement of the probe casing PC is transmitted to the tissue by pushing the transducer US against the tissue. The determination of the real movement of the US transducer against tissue is difficult due to the fact that the probe 1 is dynamically coupled also to the hand of the operator. The movement of the hand of the operator will unavoidably modify the shape of the low frequency pulse applied to the patient's body.

The present invention solves this problem by eliminating the movement of the ultrasound transducer US with respect to the probe casing PC and by measuring the position of the probe casing PC itself with a position sensor POS. The measured position is used as a feedback for the parameters of the vibrator VIB. The parameters of the vibrator VIB are then adjusted until the predefined low frequency pulse shape is obtained.

In other words, the probe 1 has no mechanical mobile external parts. The probe 1 is then an inertial probe, its movement being determined by the movement of a mass MOV placed inside the probe casing. Due to the absence of relative movement of the ultrasound transducer US with respect to the probe casing PC, measuring the amplitude of the displacement of the probe casing PC is equivalent to measuring the displacement of the ultrasound transducer US. The probe 1 is then able to directly measure the shape of the low-frequency pulse applied to the tissue and to compensate an eventual motion of the operator's hand. The absence of external moving part eliminates also the need for frequent mechanical calibration of the probe.

According to another embodiment of the present invention, the mass of the moving part MOV is equal or greater than one fourth of the total mass M of the inertial probe 1.

An advantage of this embodiment is to make it possible to effectively control the global movement of the inertial probe 1 by simply modifying the motion of the moving part MOV. In other words, if the mass of the moving part MOV was smaller its effect on the movement of the whole inertial probe 1 would be smaller, due to the momentum conservation law. The control of the motion of the tip would then be less efficient.

According to an embodiment, the US transducer is a disk shape ultrasound transducer.

An advantage of this shape is to obtain a highly symmetric emission of the ultrasound shots. The high symmetric situation simplifies the calculation of the propagation both of the ultrasound shots and of the shear wave.

According to an aspect of the invention, the force sensor FS comprises a processor suitable to calculate and to transmit the force applied to the signal generator 9.

According to an aspect of the invention, when the contact ready signal is set, the ultrasound probe 1 is constructed and arranged to lights at least one light emitting diode (LED) of said ultrasound probe 1. In fact, the lighting of a LED is used to inform the operator that the ultrasound probe 1 is correctly in contact with the patient's skin so that he stops the increase of the force applied against said patient's skin.

According to another aspect of the invention, an acoustic indicator on the signal generator 9 is constructed and arranged to indicate to the operator that the contact ready signal is set.

Besides, according to an aspect of the invention, when the contact ready signal is set, the transducer US is constructed and arranged to emit the ultrasound signals. The device commands 10 are constructed and arranged to control the frequency of ultrasound signals generated by the transducer US.

According to an embodiment the device commands 10 are also constructed and arranged to control the motion parameters of the vibrator VIB through a control loop using as a feedback the position measured by the position sensor POS.

The emission and the reception of ultrasound signals by the ultrasound transducer US of the ultrasound probe 1 enable the acquisition of a succession of images of a part of the medium to be analyzed. Thus, said production of images is only carried out when the transducer US is in contact with a to-be-measured viscoelastic medium. Moreover, the images obtained by the ultrasound transducer US are in one dimension. According to an aspect of the invention non-illustrated, the device DEV comprises a plurality of ultrasound transducers US which can be positioned in an arbitrary manner, e.g., linearly (like an echographic rod) or in a honeycomb pattern. In this manner, the device DEV permits to obtain images in 3 dimensions. Thus, the viscoelastic properties can be measured in different zones of the medium to be analyzed.

Furthermore, according to an aspect of the invention, when the contact ready signal is set, the display unit 7 also called "alphanumeric display screen" is constructed and arranged to refresh the ultrasound images. In fact, the alphanumeric display screen 7 of the ultrasound probe 1 is constructed and arranged to display the ultrasound images. The display of said images permits to assist the operator in localizing the zone in which he wants to perform the viscoelastic properties measurements.

Otherwise, according to an aspect of the invention, when the contact ready signal is set, guidance indicators are refreshed. "Guidance indicators" mean indicators displayed to the operator to assist him in the localization of the best measurement location.

Moreover, according to an aspect of the invention, when the contact ready signal is set, the device commands 10 are constructed and arranged to limit the access to at least one command of the device commands 10.

Besides, the signal generator 9 of the device DEV of the invention is constructed and arranged to emit a measurement ready signal. In fact, a too high applied force on the body can skew results of the viscoelastic properties' measurements.

According to an aspect of the invention, the measurement ready signal is determined by using the force sensor FS. In fact, a measurement ready signal is generated by the signal generator 9 when the force applied by the ultrasound probe 1 against the patient's skin is greater than a minimum measurement force threshold and smaller than a maximum measurement force threshold.

According to an aspect of the invention, the force sensor FS comprises a processor suitable to calculate and to transmit the value of the measured contact force to the signal generator 9.

According to an aspect of the invention, when the measurement ready signal is set, the ultrasound probe 1 lights at least one light emitting diode (LED). In fact, the lighting of a LED is used to inform the operator that he can generates a low frequency impulse.

According to another aspect of the invention, an acoustic indicator on the signal generator 9 is constructed and arranged to indicate to the operator the contact ready signal and/or the measurement ready signal differentiated by the type of sound.

According to an aspect of the invention, the vibrator VIB is put in motion in order to apply the low frequency pulse only if the measurement ready signal is issued by the signal generator 9. According to an embodiment the vibrator VIB is controlled by the device commands 10 based on a feedback signal provided by the position sensor POS.

More particularly, according to an aspect of the invention, the device commands 10 are constructed and arranged to control the power of the mechanical shear wave generated by the vibrator VIB on the patient's skin by controlling the electrodynamic actuator VIB. Moreover, the device commands 10 are constructed and arranged to monitor the number of shear waves generated in the medium.

Besides, according to an aspect of the invention, the electrodynamic actuator VIB, controlled by the device commands 10, is constructed and arranged to generate a transitory low-frequency impulse having a frequency range comprised between about 1 Hz and about 5000 Hz. The term "transitory low-frequency impulse" is understood to mean a mechanical stress of determined duration, the frequency of which is comprised between about 1 Hz and about 5000 Hz and the peak-to-peak amplitude of which is comprised between about 10 µm (micrometers) and about 20 millimeters, preferably between about 500 µm and about 5 mm. The duration of this stress is comprised between about 100 µs and about 20 seconds, preferably between about 5 ms and about 40 ms (milliseconds).

Thus, the electrodynamic actuator VIB, controlled by the device commands 10, permits to provide a device DEV which can produce a low-frequency vibration or stress that is perfectly controlled in time and amplitude. The form of the impulse is better controlled which enables more reliable measurements and thus an increase in the reproducibility of the system. Moreover, by means of the use of the controlled electrodynamic actuator VIB, the device DEV has a reduced volume and weight.

Moreover, as specified, the ultrasound transducer US is constructed and arranged to emit and receive ultrasound signals controlled by the device commands 10. In particular, the device commands 10 are constructed and arranged to control the range and the frequency of the emission of ultrasound signals. Simultaneously to the generation of low-frequency impulse to the patient's skin, the transducer US emits and receives ultrasound signals to track the propagation of the resulting shear wave. The tracking of said shear wave permits the measurement by determining the viscoelastic properties of the medium. In fact, shear waves have a special property: their speed depends on the viscoelastic properties of the medium through which they have been across. The harder the liver is (and therefore the higher the level of fibrosis), the faster the shear wave propagates.

Additionally, when the device DEV comprises more than one transducer, the device commands 10 allows the control of the frequencies of transducers.

Furthermore, according to an aspect of the invention, the ultrasound transducer US has an elongated shape, e.g., an oblong, rectangular, cylindrical or ellipsoid shape with a length between about 2 and about 20 millimeters, preferably about 11 millimeters, and a width between about 1 and about 10 millimeters, preferably about 5 millimeters.

According to an aspect of the invention, the ultrasound transducer US can advantageously have a conical or tapered shape with an angle between about 10 and about 80 degrees.

In addition, according to an aspect of the invention, the device commands 10 comprises a touch screen, a keyboard and optionally cursors. Moreover, the device commands 10 permits the operator to read through a display screen, also referred to as "operator interface", the information provided by the ultrasound probe 1 linked by a flexible cable 11 to the ultrasound probe 1.

In another embodiment of the invention, the device commands 10 permits deleting measurements and/or a change exam type (elastography or B-mode) and/or adding a comment or a measurement and/or changing the ultrasound gain and/or . . . .

This invention also relates to a method MET for measuring the viscoelastic properties of a viscoelastic medium having an ultrasound signal after ultrasound illumination with the device DEV described above.

Figure 4:
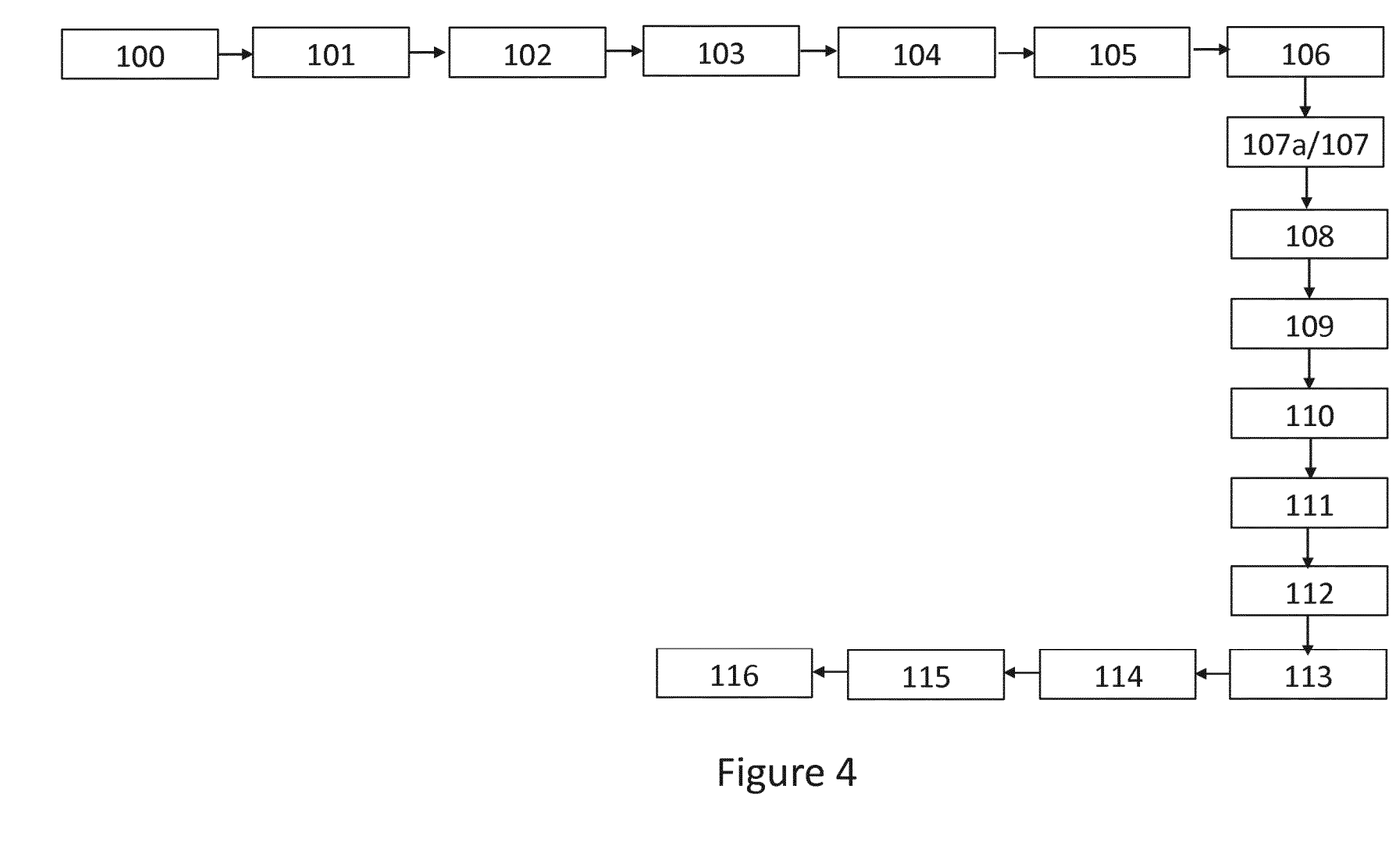
FIG. 4 represents the steps of a method for measuring the viscoelastic properties of a viscoelastic medium according to an aspect of the invention.

FIG. 4 represents an example of steps of the method MET for measuring the viscoelastic properties of a viscoelastic medium.

The method MET, as represented in the FIG. 3, comprises a positioning 100 of the ultrasound transducer US in contact with a to-be-measured viscoelastic medium.

Subsequently, the method MET comprises an application of a first force 101 by an operator against the to-be measured medium by the ultrasound probe 1. Generally, for an assessment of liver fibrosis, the ultrasound transducer US applies a force on the portion that covers the ribs.

According to another aspect of the invention, the method MET comprises a measure of the first force 102 applied by the ultrasound probe 1 against the to-be measured medium followed by a comparison of the measurement of the first force with the minimum contact force threshold. According to an aspect of the invention, the minimum force contact threshold is equal to 0.5 N.

According to another aspect of the invention the method MET comprises a step 103 of comparing the measured contact force with the maximum contact force threshold.

Then, the method MET comprises a generation of a contact ready signal 104 by the signal generator 9 based on the result of the comparison of the measured contact force with the predefined force thresholds. We remind that the contact ready signal is set when the ultrasound probe 1 is in contact with the medium to be analyzed. The contact ready signal is issued when the contact force is higher than a minimum contact force threshold. According to an embodiment the contact ready signal is issued when the contact force is comprised between a minimum and a maximum contact force threshold.

According to an aspect of the invention, the method MET comprises a step of lighting 105 at least one light-emitting diode LED of the ultrasound probe 1, said LED being lighted only when the contact ready signal is set.

According to an aspect of the invention, the method MET comprises a further step of activating the ultrasound signals 106. Thus, the ultrasound transducer US emits and receives ultrasound signals to produce images of the region of interest. We note that the ultrasound transducer US activates the emission and the reception of the ultrasound signals only when the contact ready signal is set.

According to an aspect of the invention, the method MET comprises a step 107*a* of displaying localization means only if the contact ready signal is issued. Localization means are tools used by an operator in order to locate the to-be-measured viscoelastic tissue; example of localization means are imaging, guidance tools or other indicators;

According to an aspect of the invention, the method MET comprises a step of refreshing ultrasound images 107, said ultrasound images being displayed by a display unit only when the contact ready signal is set.

According to an aspect of the invention, the method MET comprises, afterwards, a step of guidance 108 by guidance indicators, said guidance indicators being refreshed only when the contact ready signal is set.

According to an aspect of the invention, the method MET comprises, a step of limitation an access to at least one command 109 offered by the device commands 10 when the contact ready signal is set.

According to an aspect of the invention, the method MET comprises a step of activation a probe memory write 110 by the ultrasound probe 1 when the contact ready signal is set.

The method MET comprises an application of a second force 111 by the operator against the medium by the ultrasound probe 1, the second force 111 being superior to the first force 101. According to another aspect of the invention, the method MET comprises a measure of the second force applied by the ultrasound probe 1. Then, a comparison of the measurement of the second force value with the minimum measurement force threshold is realized. A comparison of the second force value with the maximum measurement force threshold can also be done.

According to an aspect of the invention, the minimum measurement force 5 threshold is equal to 4.0 N. According to an aspect of the invention, the maximum measurement force threshold is equal to 8.0 N.

According to an aspect of the invention, the method MET comprises a generation of a measurement ready signal 111 by the signal generator 9 if the measured second force is greater than a minimum measurement force threshold.

According to an embodiment of the invention the signal generator sets 111 a measurement ready signal when the measured second force is comprised between the minimum and the maximum measurement force threshold.

According to an aspect of the invention, the method comprises a step 112 of lighting at least one light-emitting diode LED of the ultrasound probe 1 when the measurement ready signal is set.

According to an aspect of the invention, the method MET comprises a step 113 of generation of a low-frequency impulse to the patient's skin. The low-frequency impulse is generated by a movement of the whole probe 1, said movement being generated by the electrodynamical actuator VIB. Said electrodynamic actuator VIB is controlled by the device commands 10. The application of the low frequency pulse according to the step 113 is triggered only if the measurement ready signal issued by the signal generator 9 is set.

According to an aspect of the invention, the method MET comprises a further step of emission and reception 114 of ultrasound signals by the ultrasound transducer US to track the propagation of the shear wave produced by the low frequency-impulse generated 113 to the patient's skin. In fact, shear waves propagation speed depends on the viscoelastic properties of the propagation medium. The harder the liver is, the faster the shear wave propagates. The displacements caused in the liver during the propagation of the shear wave are measured by ultrasound transducer US using correlation techniques on the Radio Frequency ultrasound signals.

Besides, according to an aspect of the invention, the method MET comprises a step 115 of deactivation of a combined modality of the device DEV when the contact ready signal is set. Here, a "combined modality" means another type of exam combined within the device. For instance, the combined modality is an electrocardiography ECG or a B-mode ultrasound imaging. In a non-limiting embodiment of the invention, the device DEV has two probes, one for each modality: a first ultrasound probe for elastography and a second ultrasound probe for B-mode imaging which is called the imaging probe. In that case, the contact-ready signal is used to activate or deactivate one of these probes. It is very important for security reasons to not exceed the maximum acoustic output power that is allowed for a given application. Therefore, it is important that the ultrasound signals are not emitted simultaneously by the two probes of the device DEV. Moreover using the two probes (ultrasound probe for elastography and imaging probe) simultaneously would definitively result in artefacts on both ultrasound acquisitions as signals from probes would interfere. In a non-limiting embodiment of the invention, when the contact ready signal is set, one modality is deactivated while the other modality is activated.

The method MET comprises a step of measuring the viscoelastic properties 116 of the medium analyzed as described in the US patent No 2005/0203398.

Moreover, according to an aspect of the invention, an elastic intermediary medium transparent to ultrasound (not represented in the figures) is positioned between the device DEV and the patient's skin. According to an aspect of the invention, the intermediary medium is a synthetic polymer of the polyacrylamide type. Moreover, an adhesive material or a glue can be placed between the intermediary medium and the medium under study in a manner to obtain either a sliding interface or a linked interface. Besides, the intermediary medium is innovative because it is not only transparent for ultrasound, but also for low-frequency waves. The intermediary medium is selected in a manner so as to present an elasticity close to that of the medium under study in a manner to adjust the impedance and thereby enable a maximum of energy to be transmitted to the medium under study. The intermediary medium can also be compressed such that its module of elasticity which varies in a nonlinear manner becomes close to that of the medium under study. This last proposition is moreover an original technique for measuring the elasticity of the medium: it comprises modifying the elasticity of the intermediary medium until a maximum of energy is transmitted. The elasticity attained is then close to that of the medium.

According to an aspect of the invention, the ultrasound probe 1 is used in standard echographic mode in a manner to acquire typically 20 ultrasound signals per second of the tissue or the medium. The envelope of these ultrasound signals is displayed on the alphanumeric display screen 7. The current signals are coded in gray level and in logarithmic scale to form an image called A-mode image. The signals can be placed side by side to constitute an image called M-mode image which contains the ultrasound signals acquired during a given period of time, for example 5 seconds. According to an aspect of the invention, the ultrasound probe 1 is equipped with a positioning system to know the positions at which the signals are acquired and thereby reconstitute the image of the medium to be measured when the operator slides the ultrasound probe 1 on the surface of the tissues or the medium. Besides, according to an aspect of the invention, the alphanumeric display screen 7 refreshes ultrasound images only when the contact ready signal is set. According to another aspect of the invention, the ultrasound images are only displayed at the device commands' 10 screen.

The invention claimed is:

1. A device for measuring viscoelastic properties of a viscoelastic medium having an ultrasound signal after being subjected to ultrasound pulses comprising:
    a probe for vibration controlled transient elastography comprising:
        a probe casing;
        at least one ultrasound transducer having a symmetry axis;
        a vibrator located inside the probe casing;
        a force sensor, the force sensor being configured to measure a force applied by the probe against the to-be-measured viscoelastic medium;
    a signal generator;
    wherein:
        the vibrator is arranged to induce a movement of the probe casing along a predefined axis, the predefined axis being the symmetry axis of the ultrasound transducer;
        the ultrasound transducer is bound to the probe casing with no motion of the ultrasound transducer with respect to the probe casing;
        the signal generator is constructed and arranged to issue a contact ready signal when the ultrasound transducer of the probe is in contact with a to-be-measured viscoelastic medium, the contact ready signal being set by the signal generator when the force applied by the probe on the viscoelastic medium is greater than a minimum contact force threshold.

2. The device according to claim 1, wherein the signal generator is constructed and arranged to also issue a measurement ready signal.

3. The device, according to claim 2, wherein the measurement ready signal is set by the signal generator when the force applied by the probe is greater than a minimum measurement force threshold.

4. The device according to claim 3, wherein:
    the minimum contact force threshold is comprised between 0.1 N and 1.0 N;
    the minimum measurement force threshold is comprised between 1.0 N and 6.0 N.

5. The device according to claim 3, wherein the measurement ready signal is set when the force applied by the probe on the viscoelastic medium is smaller than a maximum measurement force threshold, the maximum measurement force threshold being comprised between 6.0 N and 20.0 N.

6. The device, according to claim 3, wherein:
    the minimum contact force threshold is equal to 0.5 N;
    the minimum measurement force threshold is equal to 4 N.

7. The device according to claim 1, wherein the ultrasound transducer is bound to the probe casing by means of a probe tip, said probe tip having a first extremity fixed to the probe casing and a second extremity fixed to the ultrasound transducer.

8. The device according to claim 7, wherein the probe tip is interchangeable.

9. The device according to claim 1, wherein the probe comprises a position sensor and the device further comprises a control loop configured to control the vibrator based on the signal received from the position sensor.

10. The device according to claim 1, wherein the force sensor is a capacitive sensor or an applied force sensor.

11. The device according to claim 2, further comprising a trigger system to trigger a measurement of a viscoelastic property of a viscoelastic medium only if a measurement ready signal is set.

12. A method for measuring viscoelastic properties of a viscoelastic medium having an ultrasound signal after being subjected to ultrasound impulses, the method comprising:
providing the device of claim 1;
positioning the probe of said device such that the at least one ultrasound transducer of said probe is in contact with the to-be-measured viscoelastic medium;
generating and issuing, by the signal generator of said device, the contact ready signal when the at least one ultrasound transducer is in contact with the to-be-measured viscoelastic medium.

13. The method according to claim 12, further comprising:
measuring a force applied by the probe against the to-be-measured viscoelastic medium, the measurement of the force being determined by the force sensor of said device; and
generating and issuing, by the signal generator, a measurement ready signal, the measurement ready signal being set by the signal generator when the force applied by the probe is higher than a minimum measurement force threshold or comprised between a minimum and a maximum measurement force threshold.

14. The method according to claim 12, further comprising emitting ultrasound pulses only when the contact ready signal is set.

15. The method according to claim 12, further comprising displaying a localization tool to locate the to-be-measured viscoelastic tissue only if the contact ready signal is issued.

16. The method according to claim 12, further comprising triggering a measurement of a viscoelastic property only when the contact ready signal and the measurement ready signal are set.

17. The method according to claim 12, further comprising a step of deactivating another modality of the device when the contact ready signal is set and a step of activating another modality of the device when the contact ready signal is not set.

* * * * *